United States Patent
Sheng (10) Patent No.: US 11,376,447 B2
(45) Date of Patent: Jul. 5, 2022

(54) METHODS FOR USER ADAPTIVE RADIATION THERAPY PLANNING AND SYSTEMS USING THE SAME

(71) Applicant: The Regents of the University of California, Oakland, CA (US)

(72) Inventor: Ke Sheng, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 283 days.

(21) Appl. No.: 16/499,507

(22) PCT Filed: Apr. 5, 2018

(86) PCT No.: PCT/US2018/026297
§ 371 (c)(1),
(2) Date: Sep. 30, 2019

(87) PCT Pub. No.: WO2018/187598
PCT Pub. Date: Oct. 11, 2018

(65) Prior Publication Data
US 2021/0093891 A1    Apr. 1, 2021

Related U.S. Application Data

(60) Provisional application No. 62/481,935, filed on Apr. 5, 2017.

(51) Int. Cl.
*G16H 20/40* (2018.01)
*A61N 5/10* (2006.01)
(Continued)

(52) U.S. Cl.
CPC ......... *A61N 5/1038* (2013.01); *A61N 5/1031* (2013.01); *G06N 3/08* (2013.01); *G16H 20/40* (2018.01); *G16H 40/67* (2018.01)

(58) Field of Classification Search
CPC .... A61N 5/103; A61N 5/1038; A61N 5/1031; G06F 19/3437; G06F 19/3481;
(Continued)

(56) References Cited

U.S. PATENT DOCUMENTS 8,976,929 B2    3/2015  Wu
9,327,139 B2    5/2016  Zankowski
(Continued)

FOREIGN PATENT DOCUMENTS

CN    101268467 A    9/2008
CN    104117151 A    10/2014
(Continued)

OTHER PUBLICATIONS

International Searching Authority, International Search Report and Written Opinion for application PCT/US2018/026297, dated Jun. 28, 2018.
(Continued)

*Primary Examiner* — David P Porta
*Assistant Examiner* — Fani Polyzos Boosalis
(74) *Attorney, Agent, or Firm* — Quarles & Brady LLP (57) ABSTRACT

The present disclosure provides methods for user adaptive radiation therapy planning and a system for using the same. In some aspect, method for generating a radiation therapy plan is provided. The method includes receiving imaging information acquired from a patient and producing a preliminary radiation therapy plan, using a treatment planning system, based on the imaging information. The method also includes generating an indication for modifying the preliminary radiation therapy plan in accordance with a predetermined clinician profile, wherein the predetermined clinician profile is based on a trained learning machine. The method
(Continued)

further includes producing, using the indication, an updated radiation therapy plan that is adapted to the predetermined clinician profile.

22 Claims, 5 Drawing Sheets

(51) Int. Cl.
  *G16H 40/67* (2018.01)
  *G06N 3/08* (2006.01)
(58) Field of Classification Search
  CPC ....... G06F 19/321; A61B 5/055; A61B 6/037; A61B 6/032; G16H 50/50; G16H 40/67; G06N 3/08
  See application file for complete search history.

(56) References Cited

U.S. PATENT DOCUMENTS

| | | |
|---|---|---|
| 2007/0104316 A1 | 5/2007 | Ruchala |
| 2008/0002811 A1 | 1/2008 | Allison |
| 2010/0061510 A1 | 3/2010 | Nord |
| 2011/0130614 A1 | 6/2011 | Schulz |
| 2012/0014507 A1* | 1/2012 | Wu .......................... A61N 5/10 378/65 |
| 2013/0197878 A1 | 8/2013 | Fiege |
| 2016/0129282 A1 | 5/2016 | Yin |
| 2016/0140300 A1 | 5/2016 | Purdie |

FOREIGN PATENT DOCUMENTS

| | | |
|---|---|---|
| CN | 106029170 A | 10/2016 |
| CN | 106456993 A | 2/2017 |
| WO | 2016081916 A1 | 5/2016 |

OTHER PUBLICATIONS

Shiraishi, S. et al. "Knowledge-based prediction of three-dimensional dose distributions for external beam radiotherapy." Medical physics 43.1 (2016): 378-387.

European Patent Office. Extended European Search Report for application 18781181.5, dated Oct. 28, 2020. 9 pages.

* cited by examiner

METHODS FOR USER ADAPTIVE RADIATION THERAPY PLANNING AND SYSTEMS USING THE SAME

CROSS-REFERENCE TO RELATED APPLICATIONS

This application represents the national stage entry of International Application PCT/US2018/026297, filed on Apr. 5, 2018, which claims benefit of and priority to U.S. Application 62/481,935, filed Apr. 5, 2017, and entitled "METHODS FOR USER ADAPTIVE RADIATION THERAPY PLANNING AND SYSTEM USING THE SAME", which is incorporated herein by reference in its entirety for all purposes.

BACKGROUND

The present disclosure generally relates to systems and methods for radiation therapy planning and treatment.

Conventional external beam radiation therapy, also referred to as "teletherapy," is commonly administered using a linear accelerator ("LINAC") that produces ionizing radiation for irradiating a patient. During treatment, radiation is typically delivered to the defined target volume from several different directions, or along different beam paths. Specifically, intensity modulated radiation therapy ("IMRT") is an external beam radiation therapy technique in which the intensity, as well as the energy, of radiation beams produced by the LINAC can be independently controlled. Specifically, each beam produced by the LINAC is divided into a number of sub-beams or beamlets, whose individual intensity is varied to achieve overall beam intensity modulation. This allows various regions within target volumes, such as malignant tissues or tumors, to receive a modulated radiation dose profile. In addition, the radiation dose imparted to healthy tissues can be reduced while the dose imparted to affected tissues can be increased.

Treatment planning plays a central role in delivering radiation to a patient. In the process, an operator (typically a dosimetrist) produces a radiotherapy plan by utilizing treatment planning software designed to compute radiation dose delivered to different regions in the patient based on selected beam arrangements. By manipulating the beam properties (e.g. energy) and beam configurations (e.g. beam angle, beam number, beam intensity), a dosimetrist generally attempts to maximize radiation dose to target structures while minimizing the dose received by non-target structures. In particular, IMRT treatment planning software produces three-dimensional radiation dose maps that are specific to target shape and possibly pathology. Because of the high level of precision required for IMRT, detailed data must often be gathered about target and non-target locations and motion characteristics. In order to achieve this, accurate geometric precision is required during the treatment planning stage.

However, producing optimal radiation plans can be highly complicated, repetitive and time consuming. This is because there could be a large number of possible plan solutions for a given patient. Also, many solutions could be considered optimal from a mathematical standpoint, but satisfy very different conditions or have different trade-offs. For example, one plan may provide the best tumor coverage at the cost of higher dose to a critical organ, while another plan can do the opposite. In a different scenario, one plan can deliver a higher dose to one normal organ and sparing another, while another plan would do the opposite. As appreciated from these examples, doctors must often make clinical decision based on experience and expertise rather than objective or quantitative criteria. In addition, doctors often request multiple treatment plan revisions, putting different emphases on various clinical goals. Such iterative process of treatment planning require plan re-optimization, which can be labor and resource-intensive depending on the complexity of the treatment.

Therefore, there is a need for improved systems and methods for generating providing radiation treatment to patients.

SUMMARY

The present disclosure provides a system and methods for user adaptive radiation therapy planning that overcome the drawbacks of previous techniques. Features and advantages of the present approach will become apparent from description below.

In accordance with one aspect of the disclosure, a method for generating a radiation therapy plan is provided. The method includes receiving imaging information acquired from a patient, and producing a preliminary radiation therapy plan, using a treatment planning system, based on the imaging information. The method also includes generating an indication for modifying the preliminary radiation therapy plan in accordance with a predetermined clinician profile, wherein the predetermined clinician profile is based on a trained learning machine, and producing, using the indication, an updated radiation therapy plan that is adapted to the predetermined clinician profile.

In accordance with another aspect of the disclosure, a method for generating a trained learning machine for use in radiation treatment planning is provided. The method includes receiving a preliminary radiation therapy plan for treating a patient using radiation, and generating, based on clinical objectives, a modified radiation therapy plan using the preliminary radiation therapy plan. The method also includes determining deviations between the preliminary radiation therapy plan and the modified radiation therapy plan, and utilizing the deviations in a machine learning process to generate a trained learning machine.

In accordance with yet another aspect of the disclosure, a system for radiation therapy is provided. The system includes an input configured to receive feedback from a user, and a machine learning engine configured to receive a preliminary radiation therapy plan, and generate, based on the preliminary radiation therapy plan, an updated radiation therapy plan using feedback from the user. The machine learning algorithm is also configured to determine deviations between the preliminary radiation therapy plan and the updated radiation therapy plan, and apply the deviations in a machine learning process to generate a trained learning machine. The machine learning algorithm is further configured to generate a user profile corresponding to the trained learning machine. The system also includes an output for providing a report in accordance with the user profile.

DETAILED DESCRIPTION

Radiation treatment planning often utilize iterative and labor-intensive processes to generate optimized plans that satisfy treatment and clinical goals. Over time, some efficiencies can develop when dosimetrists get familiar with a doctor's preferences. This is often referred to as "a bond" between the doctor and dosimetrist, which allows an acceptable plan to be achieved more quickly. Despite this, it is recognized herein that current clinical workflows present at least two lost opportunities. First, personnel turnover often break doctor-dosimetrist bonds, and time would be needed to form others. Furthermore, there are no guarantees that new bonds would work as well. Second, in-house knowledge regarding specific treatments may not be readily quantifiable or transferable. For instance, a large institution specializing in head and neck cancer treatment would be able to provide high quality treatment because resources are available to develop optimal treatment protocols. By contrast, a community hospital or small clinic might not be able to do as well, or benefit from such large institution in-house knowledge. This is because small clinics receive patients with all kinds of cancer diagnoses, and would not have the time or resources to be specialized in the treatment of any one disease.

Therefore, the present disclosure provides a system and methods that address current clinical workflow needs. Specifically, a novel adaptive radiation therapy planning approach based on machine learning is introduced herein, which takes advantage of knowledge gained by clinicians during planning processes. As described, the ability to capture planning information and provide treatment planning adaptive to specific oncologists, disease types, and so on, would be tremendously efficient and beneficial to treating patients. As appreciated from descriptions below, the present approach can be used to streamline treatment planning workflows, reduce costly and time-consuming redundancies, and achieve enhanced plan consistencies.

Figure 1:
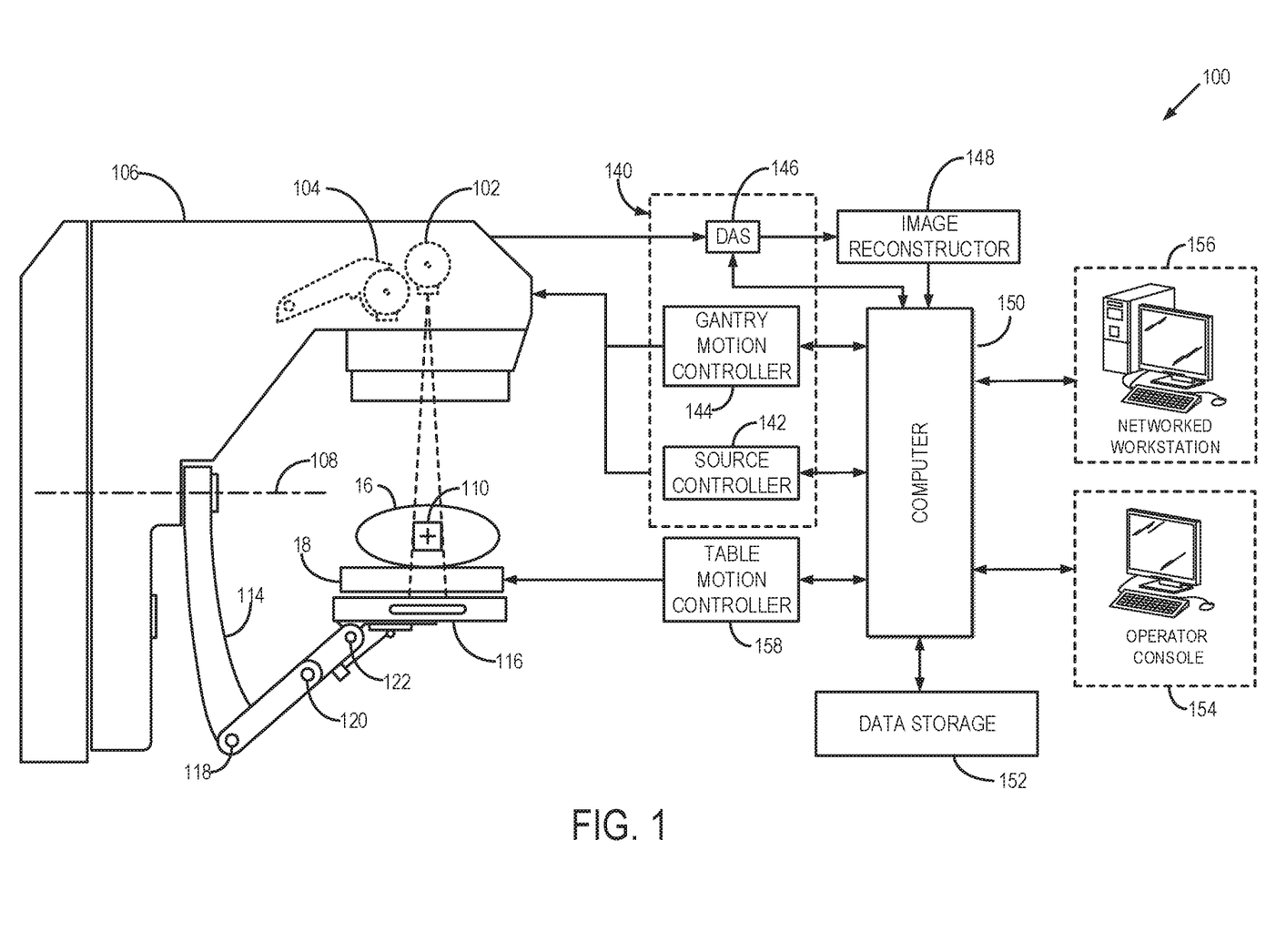
FIG. 1 is a block diagram of an example radiation therapy system, in accordance with aspects of the present disclosure.

Referring to FIG. 1, an example radiation therapy system 100, in accordance with aspects of the present disclosure, is shown. The system 100 includes a therapeutic radiation source 102 for producing radiation, such as x-ray or electron radiation. The system 100 may also include a diagnostic x-ray source 104, or the diagnostic x-ray source 104 may be foregone in favor of an imaging system. If included, the diagnostic x-ray source 104 is configured to project a cone-beam of x-rays toward an x-ray detector 116 comprising an array of detectors.

Both the therapeutic radiation source 102 and diagnostic x-ray source 104 are attached adjacent each other and housed at the same end of a first rotatable gantry 106, which rotates about a pivot axis 108. The first rotatable gantry 106 allows either of the therapeutic radiation source 102 and diagnostic x-ray source 104 to be aligned in a desired manner with respect to a target volume 110 in a subject 16 positioned on a patient table 18. A second rotatable gantry 114 is rotatably attached to the first rotatable gantry 106 such that it too is able to rotate about the pivot axis, 108. Disposed on one end of the second rotatable gantry 114 is an x-ray detector 116. The x-ray detector 116 can function not only as a diagnostic image device when receiving x-rays from the diagnostic x-ray source 104, but also as a portal image device when receiving x-rays from the therapeutic radiation source 102.

The x-ray detector 116 is formed by a number of detector elements that together sense the projected x-rays that pass through the subject 16. Each detector element produces an electrical signal that represents the intensity of an impinging x-ray beam and, hence, the attenuation of the beam as it passes through the subject 16. The second rotatable gantry 114 further includes an articulating end that can pivot about three points 118, 120, and 122. The pivoting motion provided by these points 118, 120, and 122, allows the x-ray detector 116 to be moved within a two-dimensional plane.

The rotation of the rotatable gantries, 106 and 114, and the operation of the radiation sources, 102 and 104, are governed by a control mechanism 140 of the system 100. The control mechanism 140 includes a source controller 142 that provides power and timing signals to the radiation sources, 102 and 104, and a gantry motor controller 144 that controls the rotational speed and position of the gantries, 106 and 114. A data acquisition system ("DAS") 146 in the control mechanism 140 samples analog data from detector elements and converts the data to digital signals for subsequent processing. An image reconstructor 148, receives sampled and digitized x-ray data from the DAS 146 and performs high speed image reconstruction. The reconstructed image(s) may be provided as input to a computer 150 which can store the image(s) and other information in a data storage 152. By way of example, the data storage 152 may be a local data storage location, such as a hard drive, or a remote data location, such as a data storage server, database, PACS, and so forth. The computer 150 may also retrieve data and information from the data storage 152.

The computer 150 also receives commands and scanning parameters from an operator via an operator console 154 having various input elements, such as a keyboard, mouse, touchscreen and the like. The operator console 154 also includes a display that allows the operator to observe reconstructed images, treatment status and other data from the computer 150. The operator supplied commands and parameters are used by the computer 150 to provide control signals and information to the DAS 146, the source controller 142 and the gantry motor controller 144. In addition, the computer 150 operates a table motor controller 158 which controls the motorized patient table 18 to position the subject 16 within the gantries, 106 and 114.

As shown, the computer 150 may also be in communication with at least one networked workstation 156, which may be a treatment planning station. In this case, the computer 150 may receive and coordinate execution of a radiation therapy plan generated using the networked workstation 156. The network workstation 156, whether within the same facility or in a different facility as the operator console 154, may also gain remote access to the data storage 152, the image reconstructor 148, either directly, via the computer 150, using various communication systems. In this manner, x-ray data, reconstructed images, or other information or data may be exchanged between the data storage 152, the computer 150, the image reconstructor 148, and the networked workstation 156, such that the data or images may be remotely processed by the networked workstation 156. This data may be exchanged in any suitable format, such as in accordance with the transmission control protocol ("TCP"), the Internet protocol ("IP"), or other known or suitable protocols.

Figure 2:
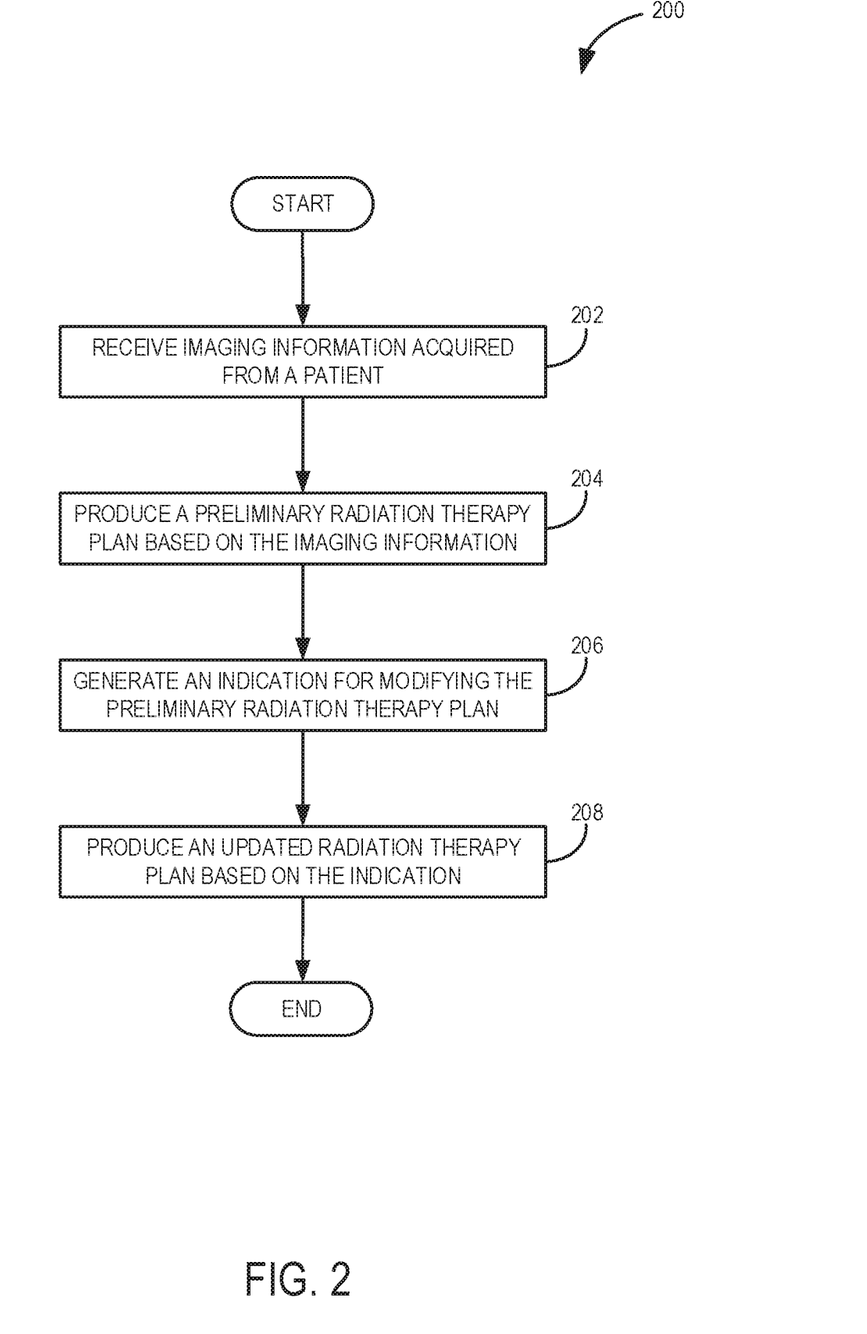
FIG. 2 is a flowchart setting forth steps of a process, in accordance with aspects of the present disclosure.

Turning now to FIG. 2, a flowchart setting forth steps of a process 200 for generating a radiation therapy plan, in accordance with aspects of the present disclosure, is shown. The process 200 may be carried out using any suitable device, apparatus or system, such as a treatment planning station. In some implementations, the process 200 may be carried out using, or in cooperation with, the system described with reference to FIGS. 1 and 4. In particular, steps of the process 200 may be performed using at least one processor configured to execute programming or instructions stored in non-transitory computer readable media. The processor may be a general-purpose processor. Alternatively, the processor may be a dedicated or application-specific processor having non-transitory programming or executable instructions hardwired therein.

The process 200 may begin at process block 202 with receiving imaging information acquired from a patient. The imaging information received may be in a variety of formats, and be acquired during various image studies or simulations. For example, imaging information may include computed tomography ("CT") images, magnetic resonance ("MR") images, positron emission tomography ("PET") images, and others. In some aspect, patient information may also be provided at process block 202, such as the patient characteristics (e.g. gender, age, body shape and size), patient medical condition (e.g. performance status) and medical history (e.g. prior chemotherapy, radiation and other treatment history), contraindications, patient implant information, geometrical information of target and non-target structures (e.g. shapes, sizes, and absolute/relative positioning), and so forth.

Then, at process block 204, a preliminary radiation therapy plan, satisfying clinical objectives, may be produced using the imaging and other information received. Example clinical objectives may include achieving various prescription doses for target and non-target structures, minimizing treatment time, and others. To produce the preliminary radiation therapy plan, various planning tools and optimization techniques known in the field may be utilized.

At process block 206, an indication for modifying the preliminary radiation therapy plan may then be generated. The indication may be obtained based on a predetermined or selected clinician profile and patient information, and recommend, as well as apply, specific modifications for the preliminary radiation therapy plan. As described herein, the clinician profile may be generated using learning machine that is trained to reflect treatment configuration and preferences of a dosimetrist, an oncologist, or other clinician. For example, the indication generated according to the predetermined clinician profile may suggest position modifications for certain isodose lines or changes in beam configurations likely found to be acceptable by the clinician.

Then, at process block 208, an updated radiation therapy plan adapted to the predetermined clinician profile may be produced using the indication. The updated plan be produced manually by a user responding to the indication. For instance, a user or clinician may choose to accept or reject the suggestions provided. Alternatively, the suggestions may be automatically implemented to produce the updated plan. In this case, a user or clinician may also have the option of adjusting the automatically implemented suggestions. In some aspects, deviations or differences between the preliminary radiation therapy plan and the updated radiation therapy plan may be determined at process block 208. Such deviations, along with patient and user information, may be used to update the trained learning machine.

In some aspects, a report may also be generated at process block 208. The report may be in any form and provide any information. For instance, the report may be indicative of the updated plan or indicate differences relative to the preliminary plan. In some implementations, the report may be directed to a radiation therapy system.

Figure 3:
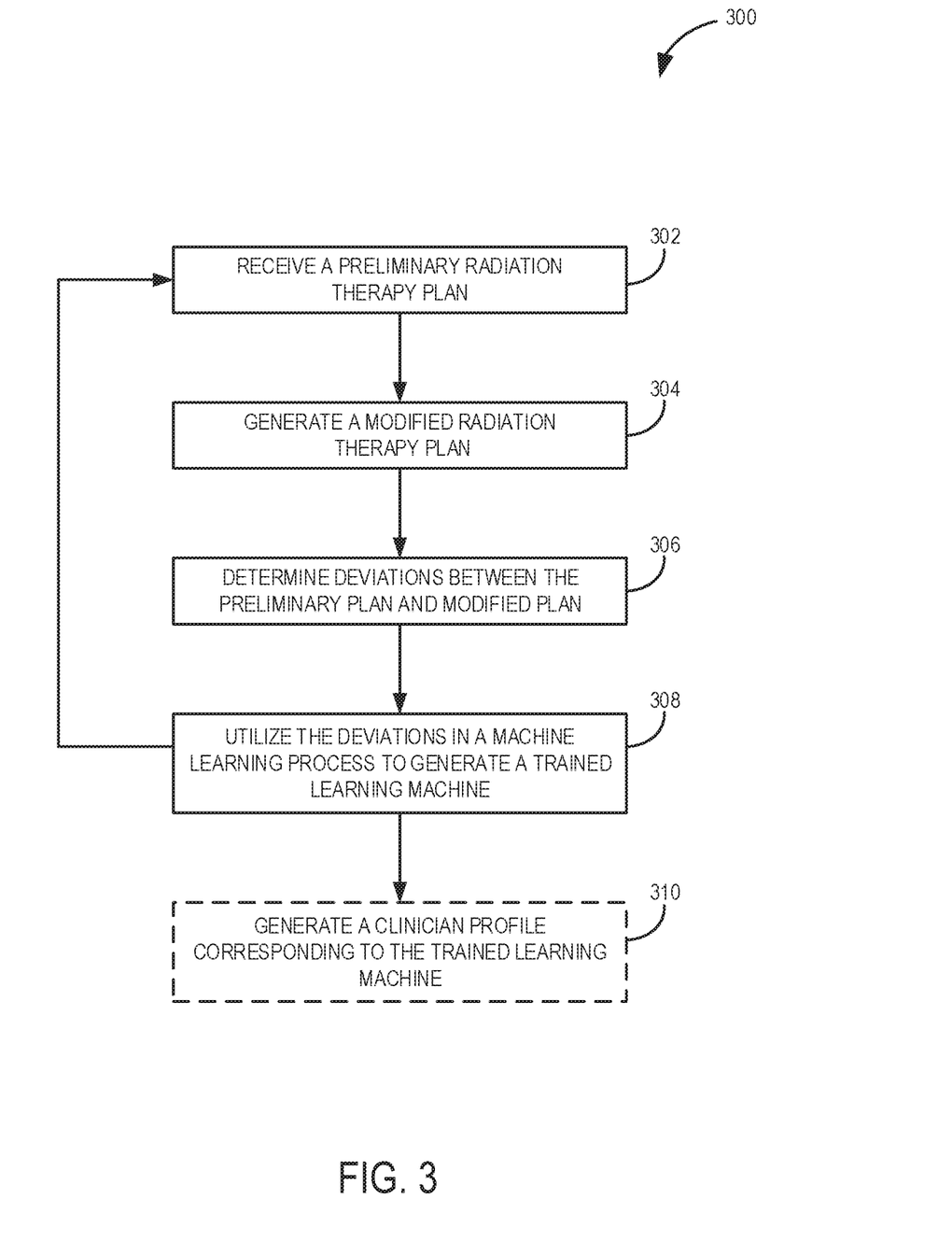
FIG. 3 is another flowchart setting forth steps of a process, in accordance with aspects of the present disclosure.

Turning now to FIG. 3, a flowchart setting forth steps of a process 300, in accordance with aspects of the present disclosure. As above, steps of the process 300 may be carried out using any suitable device, apparatus or system, including using, or in cooperation with, a system as described with reference to FIGS. 1 and 4. In particular, steps of the process 300 may be performed using at least one processor configured to execute programming or instructions stored in non-transitory computer readable media. The processor may be a general-purpose processor. Alternatively, the processor may be a dedicated or application-specific processor having non-transitory programming or executable instructions hardwired therein. In one example, steps of the process 300 may be carried out by a machine learning engine of a treatment planning system or workstation.

The process 300 may begin at process block 302 with receiving a preliminary radiation therapy plan of a patient. In some aspects, the preliminary plan may be accessed or retrieved from a memory, or other data storage location. Alternatively, the plan may be generated manually, automatically or semi-automatically by a clinician or user.

Figure 5:
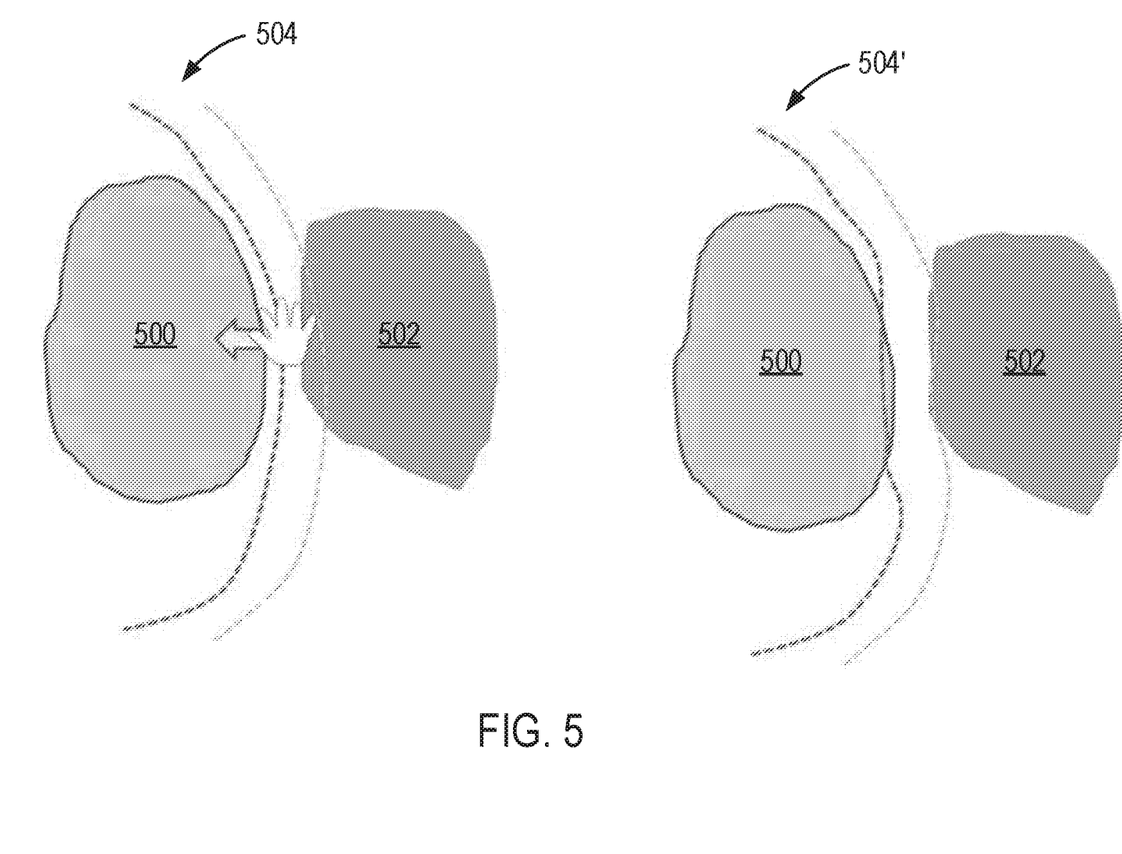
FIG. 5 is a graphical illustration showing modification of a treatment plan, in accordance with aspects of the present disclosure.

Then, based on various clinical objectives, a modified radiation therapy plan may be generated at process block 304 using or based on the preliminary plan. To this end, a treatment planning system, for instance, may be configured to enable a direct interaction between a user or clinician and software, allowing such plan modifications. In some implementations, envisioned functionality may allow a user to drag or modify the position of various isodose lines in order to reduce the hot or cold spot at certain locations in the patient. FIG. 5 illustrates one non-limiting example of such functionality. Specifically, a first region 500 (e.g. a tumor tissue), a second region 502 (e.g. a non-tumor tissue), and a set of isodose lines 504 corresponding to the first region 500 are shown. These regions may be identified by a user or clinician as particularly important to plan quality. As shown, the position of the isodose lines 504 may be modified by the user to generate modified isodose lines 504'. Depending on the position of the modified isodose lines 504', radiation dose received by these different regions may increase or decrease. In some implementations, the plan may then be re-optimized instantaneously, giving the user real-time information in accordance with modifications being made. However, plan changes need not be limited to modifying the position of 2D isodose lines as illustrated in FIG. 5. For instance, a set of 3D tools can also be utilized, allowing a user to interact with one or more 3D isodose surfaces for improved efficiency. In other functionalities, the user may also be able modify beam configurations, as well as other plan parameters.

Referring again to FIG. 3, at process block 306, deviations between the preliminary radiation therapy plan and the modified radiation therapy plan may be determined. For example, differences between positions of specific isodose lines may be identified and recorded. Such deviations, and other plan modifications, along with patient information and user/clinician information, may then be used in a machine learning process to generate a trained learning machine, as indicated by process block 308. The training may be carried out using a convolutional neural network algorithm, a support vector machine algorithm or Bayesian optimization, and other techniques. In some implementations, the learning machine may be trained to minimize differences between proposed doses (e.g. associated with preliminary plans) and accepted doses (e.g. associated with modified plans) of predetermined or selected structures. A clinician/user profile corresponding to the trained learning machine may then be optionally generated, as indicated by process block 310. In some aspects, the trained learning machine may be specifically configured to reflect specific diseases or conditions. To this end, one or more disease profiles may also be generated. Learned planning knowledge captured by such clinician/user and disease profiles may then be shared between different institutions, and may be updated based on clinical practice.

As shown, process blocks 302-308 may be repeated a number of times. In this manner, the learning machine can be updated and retrained. In addition, the process of training the learning machine may utilize information from more than one patient. In some aspects, such training can be performed completely automatically during normal clinical workflow associated with treatment planning. A criterion can be set to determine if a knowledge base is "mature" for clinical deployment. The trained learning machine can then be used to guide the planning for various groups of patients, across a single or multiple institutions and clinicians. To this end, patient and user, or clinician information, may be shared among various departments and institutions. As described, the trained learning machine may be used to provide an indication for generating radiation therapy plans.

Figure 4:
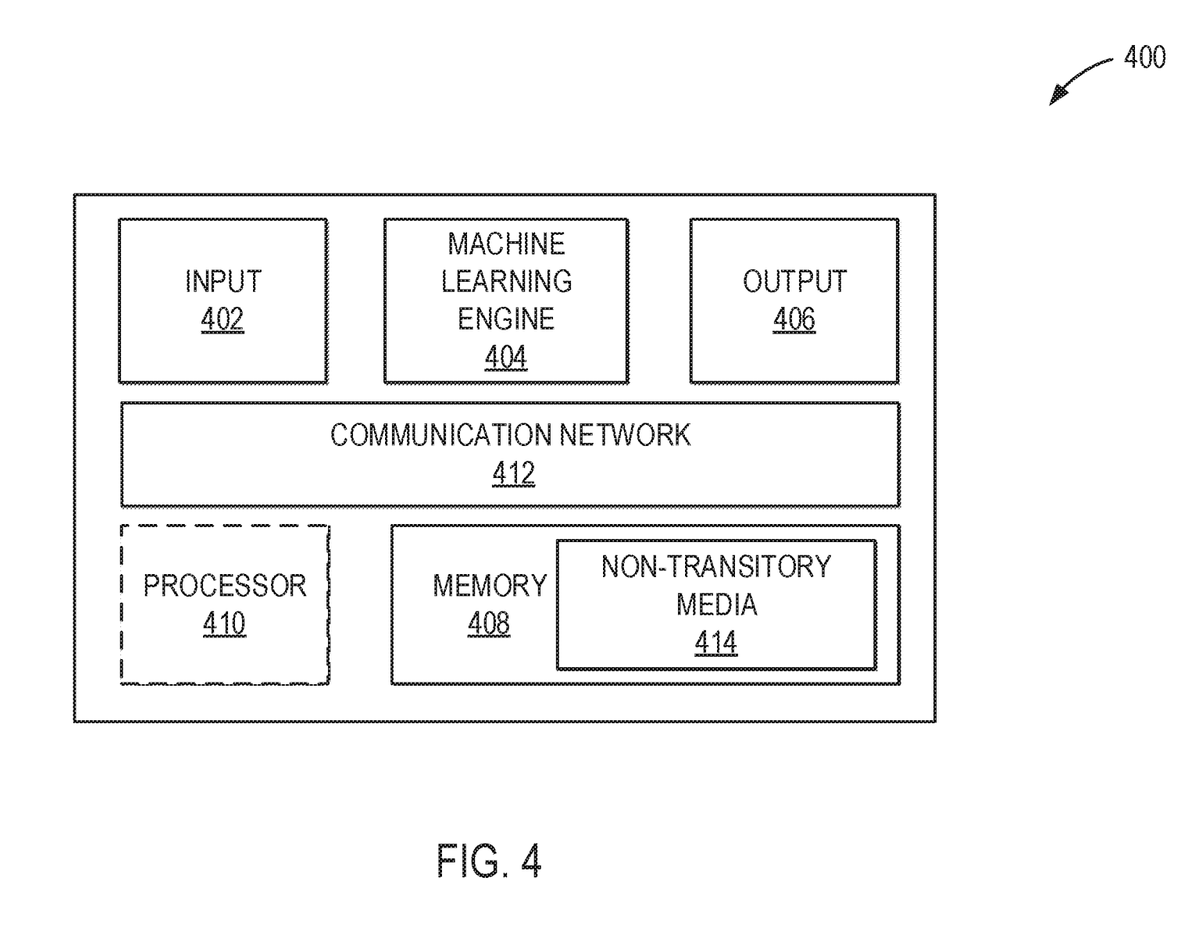
FIG. 4 is a block diagram of an example system, in accordance with aspects of the present disclosure.

Referring now to FIG. 4, a system 400 in accordance with aspects of the present disclosure is shown. In some applications, the system 400 may be a treatment planning system. In general, the system 400 includes an input 402, a machine learning engine 404, an output 406, a memory 408, and optionally a separate processor 410. The system also includes a communication network 412 configured to facilitate the transfer of data, signals and other information between the various elements of the system 400.

The input 402 is configured to receive input and feedback from a user and may include various elements such as a mouse, a keyboard, buttons, switches, toggles, knobs, touch screens, or other touch-responsive elements, as well as ports, connectors, and receptacles for flash-memory, USB sticks, cables, and so on.

The machine learning engine 404 may include various components hardware for carrying out methods in accordance with the present disclosure. For example, the machine learning engine 404 may include a central processing unit ("CPU") with one or more cores, and optionally a graphical processing unit ("GPU"). In some implementations, the machine learning engine 404 is programmed to receive or access a preliminary radiation therapy plan and generate an updated radiation therapy plan using feedback provided by a user via the input 402. The machine learning engine 404 may then determine deviations between the preliminary radiation therapy plan and the updated radiation therapy plan, and apply the deviations in a machine learning process to generate a trained learning machine. In the machine learning process, the machine learning engine 404 may apply a convolutional neural network algorithm, a support vector machine algorithm or a Bayesian optimization algorithm, as well as utilize patient information, as described.

In some implementations, the machine learning engine 404 may generate various clinician/user profile and disease profiles, corresponding to the trained learning machine(s), and provide a report, in accordance with such profiles, via the output 406. As described, the clinician/user and disease profiles may be applied in various treatment planning processes, providing indications for preparing or updating radiation therapy plans. In addition, the ability to share learned planning knowledge is highly advantageous. To this end, knowledge captured by the trained learning machines may be remotely accessible, and updated based on clinical practice or experience.

The output 406 may be configured to provide a report by way of various output elements, including screens, displays, LEDs, LCDs, speakers and so on.

The memory 408 may include various memory elements where a number of types of data (e.g., internal data, external data instructions, software codes, status data, diagnostic data, etc.) may be stored. As an example, the memory 112 may include random access memory ("RAM"), dynamic random access memory ("DRAM"), electrically erasable programmable read-only memory ("EEPROM"), flash memory, and the like. In some implementations, the memory 408 may also include non-transitory computer-readable media 414, which may include instructions for operating the system 400 and carrying out steps of methods in accordance with present disclosure. The memory 408 may store various information including patient information, user or clinician profiles and information, treatment plan information, and so forth.

The communication network 412 may include a variety of communication capabilities and circuitry, including various wiring, components and hardware for electronic, radiofrequency ("RF"), optical and other communication methods. By way of example, the communication network 412 may include parallel buses, serial buses, and combinations thereof. Example serial buses may include serial peripheral interface (SPI), I2C, DC-BUS, UNI/O, 1-Wire, and others. Example parallel buses may include ISA, ATA, SCSI, PIC, IEEE and others.

The present invention has been described in terms of one or more preferred embodiments, and it should be appreciated that many equivalents, alternatives, variations, and modifications, aside from those expressly stated, are possible and within the scope of the invention.

What is claimed is:

1. A method for generating a radiation therapy plan, the method comprising:
   receiving imaging information acquired from a patient;
   producing a preliminary radiation therapy plan, using a treatment planning system, based on the imaging information;
   generating an indication for modifying the preliminary radiation therapy plan in accordance with a predetermined clinician profile, wherein the predetermined clinician profile is based on a trained learning machine; and
   producing, using the indication, an updated radiation therapy plan that is adapted to the predetermined clinician profile.

2. The method of claim 1, wherein the method further comprises generating the indication using patient information.

3. The method of claim 1, wherein the method further comprises determining deviations between the preliminary radiation therapy plan and the updated radiation therapy plan.

4. The method of claim 3, wherein the method further comprises updating the trained learning machine corresponding to the predetermined clinician profile using the deviations.

5. The method of claim 4, wherein the method further comprises updating the trained learning machine using at least one of patient information and user information.

6. A method for generating a trained learning machine for use in radiation treatment planning, the method comprising:
   receiving a preliminary radiation therapy plan for treating a patient using radiation;
   generating, based on clinical objectives, a modified radiation therapy plan using the preliminary radiation therapy plan;
   determining deviations between the preliminary radiation therapy plan and the modified radiation therapy plan; and
   utilizing the deviations in a machine learning process to generate a trained learning machine.

7. The method of claim 6, wherein the method further comprise utilizing patient information to generate the trained learning machine.

8. The method of claim 7, wherein the patient information comprises patient characteristics, medical history, shape, size and positioning of target and non-target structures, or a combination thereof.

9. The method of claim 7, wherein the method further comprises utilizing patient information from a plurality of patients to generate the trained learning machine.

10. The method of claim 6, wherein the method further comprises modifying at least one isodose line or at least one isodose surface to generate the modified radiation therapy plan.

11. The method of claim 6, wherein the method further comprises applying a convolutional neural network algorithm, a support vector machine algorithm or a Bayesian optimization algorithm to generate the trained learning machine.

12. The method of claim 6, wherein the method further comprises training the trained learning machine to minimize a difference between a proposed dose and an accepted dose of at least one selected structure.

13. The method of claim 6, wherein the method further comprises generating at least one of a clinician profile and disease corresponding to the trained learning machine.

14. The method of claim 13, wherein the method further comprises providing an indication in accordance with the clinician profile to generate a radiation therapy plan.

15. The method of claim 6, wherein the method further comprises providing remote access to the trained learned machine.

16. The method of claim 15, wherein the method further comprises updating the trained learning machine based on clinical practice.

17. A system for radiation therapy, the system comprising:
   an input configured to receive feedback from a user;
   a machine learning engine configured to:
      receive a preliminary radiation therapy plan;
      generate, based on the preliminary radiation therapy plan, an updated radiation therapy plan using feedback from the user;
      determine deviations between the preliminary radiation therapy plan and the updated radiation therapy plan;
      apply the deviations in a machine learning process to generate a trained learning machine; and
      generate a user profile corresponding to the trained learning machine; and
   an output for providing a report in accordance with the user profile.

18. The system of claim 17, wherein the machine learning engine is further configured to apply the user profile in a treatment planning process generating plans to treat patients using radiation.

19. The system of claim 17, wherein the machine learning engine is further configured to utilize patient information to generate the trained learning machine.

20. The system of claim 17, wherein the machine learning engine is further configured to apply a convolutional neural network algorithm, a support vector machine algorithm or a Bayesian optimization algorithm to generate a trained learning machine.

21. The system of claim 17, wherein the machine learning engine is further configured to generate a clinician profile corresponding to the trained learning machine.

22. The system of claim 17, wherein the system is further configured to provide an indication, in accordance with the user profile, for use in preparing a radiation therapy plan.

* * * * *